(12) United States Patent
Mezzoli et al.

(10) Patent No.: US 6,569,090 B1
(45) Date of Patent: May 27, 2003

(54) APPARATUS FOR SELF-INSPECTING THE EAR

(75) Inventors: Giorgio Mezzoli, Via Ricci Curbastro, 56/1, 48022 Lugo (Prov. of Ravenna) (IT); Marco Vanzi, Bologna (IT)

(73) Assignee: Giorgio Mezzoli, Prov. of Ravenna (IT)

( * ) Notice: Subject to any disclaimer, the term of this patent is extended or adjusted under 35 U.S.C. 154(b) by 0 days.

(21) Appl. No.: 09/889,247

(22) PCT Filed: Jan. 11, 2000

(86) PCT No.: PCT/EP00/00128
§ 371 (c)(1),
(2), (4) Date: Jul. 11, 2001

(87) PCT Pub. No.: WO00/41616
PCT Pub. Date: Jul. 20, 2000

(30) Foreign Application Priority Data

Jan. 12, 1999 (IT) .......................................... MI99A0036

(51) Int. Cl.⁷ .............................................. A61B 1/227
(52) U.S. Cl. ........................ 600/200; 600/246; 606/18; 606/19
(58) Field of Search ................................ 600/200, 245, 600/246, 248, 249; 606/18, 19

(56) References Cited

U.S. PATENT DOCUMENTS 2,943,184 A    6/1960    Christopherson
4,925,285 A  * 5/1990    Dowdell et al. ............ 600/200
5,501,652 A    3/1996    Woods ....................... 600/200

FOREIGN PATENT DOCUMENTS

EP    0 012 817    12/1978
FR    2 380 763     9/1978

OTHER PUBLICATIONS

PCT International Preliminary Examination Report.

* cited by examiner

Primary Examiner—John P. Leubecker
Assistant Examiner—Jocelyn Debra Ram
(74) Attorney, Agent, or Firm—Abelman, Frayne & Schwab

(57) ABSTRACT

Ear observation apparatus for self-inspecting the external auditory meatus and/or the tympanic membrane, characterized in that it comprises inspection means (2) for the external auditory meatus associated to reflection means (3) able to reflect the image of said external auditory meatus and/or tympanic membrane, illumination means (6) being provided for illuminating said external auditory meatus and/or tympanic membrane, said reflection means (3) being angularly set with respect to said inspection (2) means such as to reflect the image of the external auditory meatus and/or tympanic membrane on an external mirror.

9 Claims, 3 Drawing Sheets

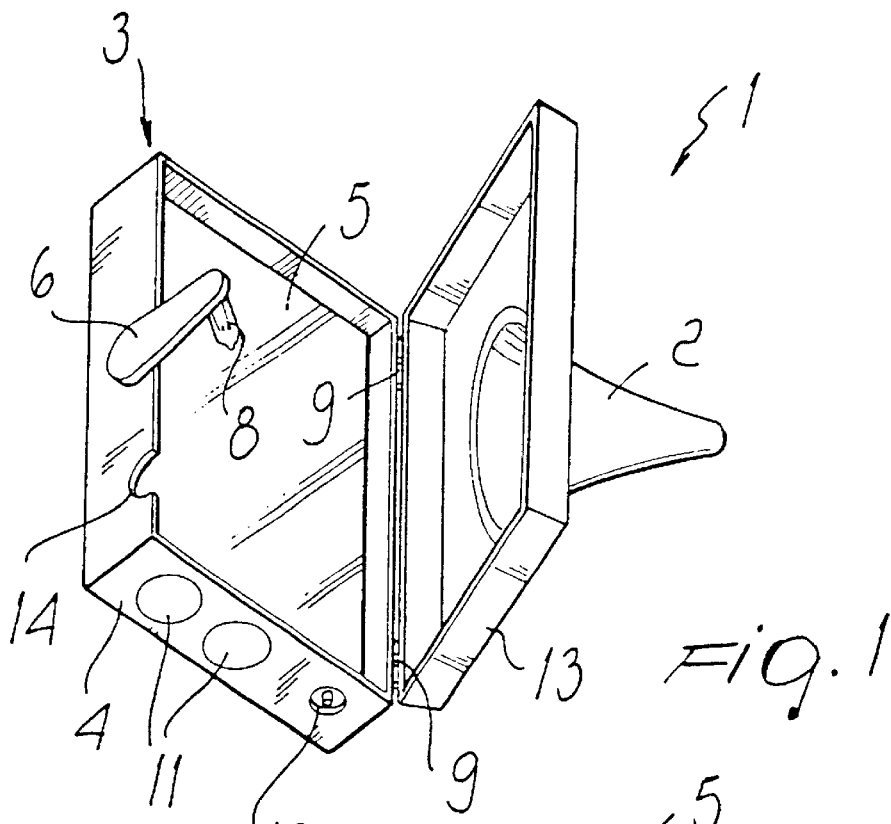
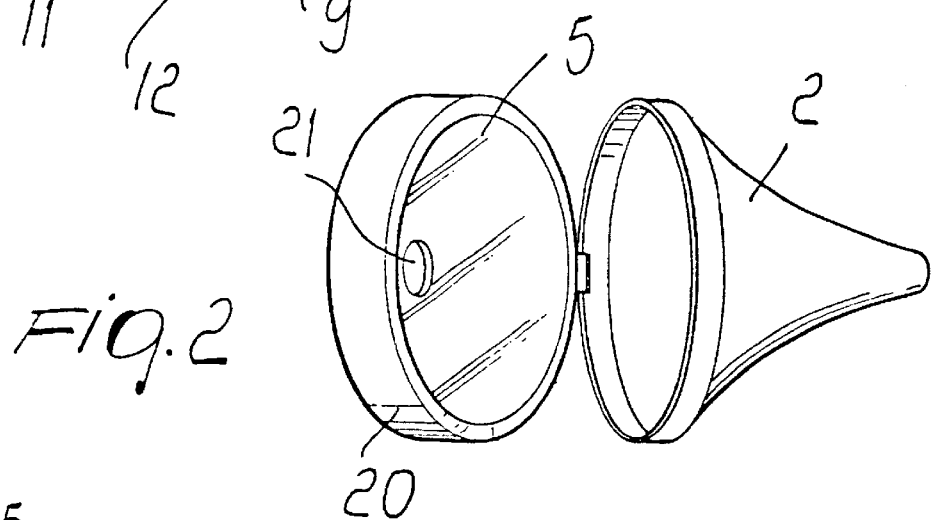
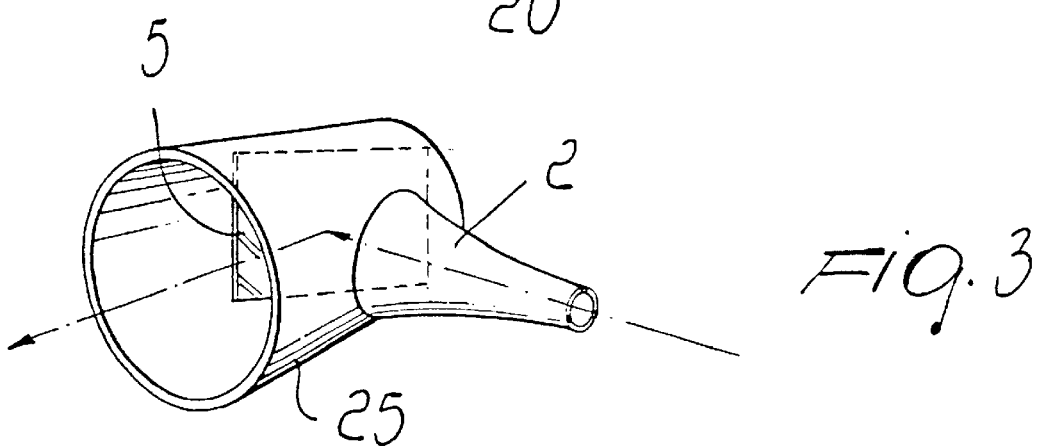

APPARATUS FOR SELF-INSPECTING THE EAR

TECHNICAL FIELD

The present invention relates to an apparatus for self-inspecting the external auditory meatus. More particularly, the invention relates to an apparatus for self-inspecting the external auditory meatus (E.A.M.) and/or the tympanic membrane (T.M.).

BACKGROUND ART

As known, the distal portion of the external auditory meatus begins from the pinna which is the portion of the ear externally visible on the head of the subject, and ends on the tympanic membrane at its proximal portion, where the so-called middle ear begins. Thus the external auditory meatus is a part of the external ear and has a filter-like action as the ratio between the sound pressures at the tympanic membrane and at the entrance of the external auditory meatus varies with the frequency, i.e. the pressure increase is null until a given frequency, then grows and then decreases. The top frequency is in the maximal sensitivity zone of the audition and the external auditory meatus contributes thereto. The peculiar anatomic conformation of the auditory meatus and the orthogonal positions between eves and ears makes practically impossible to self-inspect the external auditory meatus and the tympanic membrane, particularly for hygienic purpose. In fact, contrarily to other parts of the body, the cleaning of the external auditory meatus is carried out without directly looking the anatomic area which is involved by the operation, thus the results of such a cleaning are not safely optimal as they cannot be easily checked. Indeed, while for the cleaning of other body parts the immediate vision can confirm the positive result of the cleaning itself and opportunely lead in a corrective action, in the case of the ear, and particularly of the external auditory meatus, the cleaning procedures are effected blindly as it is impossible to check the meatus and thus the total removal of the physiological and unaesthetic cerumen aggregates in the distal portion, and to inspect the formation of plugs in the proximal portion.

Furthermore the blindly effected cleaning procedure can be dangerous both for the external auditory meatus and the tympanic membrane.

The formation of cerumen plugs may yield an annoying and pathologic auditory faculty decrease with a consequent need of specialized ambulatory checkup, where precise apparatus for inspecting the external auditory meatus and the tympanic membrane are employed for directing the tools useful for the plug removal.

It is anyway apparent that this implies a lack of self-sufficiency of the single subjects which are compelled to ask the help of specialized structures and persons.

U.S. Pat. No. 4,925,285 discloses an apparatus for the anatomical self-examination made of a support frame for a system of mirrors which, suitably oriented, provide a wide vision of a recumbent subject. Setting apart the big dimensions of such an apparatus, it is clear that its scope can be mainly esthetical or, anyway, cannot be directed to a close-up self-inspection of an area such that of the ear.

U.S. Pat. No. 5,501,652 illustrates a self-examination otoscope for the eardrum and external canal made as an elongated body endowed with an eyepiece at one end and a speculuni at the other. An internal light illuminates the organ the image of which is reflected in a three mirrors system to reach the subject's eye.

SUMMARY OF THE INVENTION

The main scope of the present invention is providing an apparatus for self-inspecting the external auditory meatus and/or the tympanic membrane, thus avoiding the need of cleaning of such meatus by a specialized center.

This scope is accomplished by providing an apparatus for self-inspecting the external auditory meatus and/or the tympanic membrane, which allows the subject to easily check the cleaning conditions of the external auditory meatus and/or the tympanic membrane, and the result of the effected cleaning, thus also avoiding the risk of the use of inappropriate tools for such a cleaning.

Another advantage of the present invention is providing an apparatus for self-inspecting the external auditory meatus of the ear, having small dimensions and which is easy for the user to carry around.

A further advantage of the invention is providing an apparatus for self-inspecting the external auditory meatus just requiring a mirror to stay in front of for its use.

Last but not least, the present invention provides an apparatus for self-inspecting the external auditory meatus endowed with high reliability, rather easy to be manufactured and having a competitive price.

These advantages, and others which will become apparent hereinafter, are accomplished by an apparatus for self-inspecting the external auditory meatus and/or the tympanic membrane comprising inspection means for inspecting the external auditory meatus, associated to reflection means for casting back the image of said external auditory meatus and/or said tympanic membrane, to illumination means for lighting said external auditory meatus and/or said tympanic membrane, and said reflection means are angularly set with respect to said inspection means such as to reflect on an external mirror the image of said external auditory meatus and/or said tympanic membrane.

BRIEF DESCRIPTION OF THE DRAWINGS

Further characteristics and advantages of the finding will become more apparent from the description of the preferred, but not limiting embodiments of the apparatus according to the invention, representatively but not limitedly illustrated in the enclosed drawings wherein FIG. 1 is a perspective view of a first embodiment of the apparatus of the present invention;

FIG. 2 shows a perspective view of a second embodiment of the apparatus of the present invention;

FIG. 3 shows a perspective view of a third embodiment of the apparatus of the present invention;

DESCRIPTION OF THE PREFERRED EMBODIMENTS

Figure 4A:
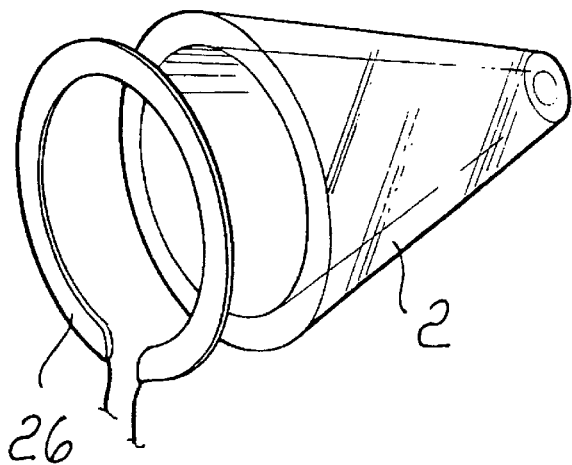
FIG. 4a shows a first variant of a detail of FIGS. 1, 2 and 3.

Referring to the above mentioned figures, wherein the same reference numbers relate to the same elements, the apparatus for self-inspecting the external auditory meatus and/or the tympanic membrane, globally indicated by the reference number 1, comprises, in a first embodiment shown in FIG. 1, inspection means for the external auditor meatus and/or the tympanic membrane, suitably made of a speculum 2 which is pivoted to reflection means of the image captured through the speculum, such reflection means being pointed by the reference number 3.

The reflection means 3 are suitably made of a box shaped body 4 harboring at least one mirror 5 and provided with illumination means 6 with a lamp 8 beaming a light which is reflected by said mirror 5.

By the mirror 5 said illumination means 6 are intended for illuminating the speculum 2 and, through the pipe thereof, the external auditory meatus and/or the tympanic membrane, thus allowing the subject to clearly see the external auditory meatus and/or the tympanic membrane. This is one of the feature distinguishing the present apparatus from that disclosed by U.S. Pat. No. 5,501,652. As already said above the apparatus of the prior art provides illumination means directly oriented to the anatomic portion to illuminate, whereas the apparatus of the invention provides the indirect illumination of the external auditory meatus and/or of the tympanic membrane as the light is directed to the mirror which reflects it into the organ and contemporaneously cast back the image. Such an indirect illumination is more diffused and yields a clearer and better vision of the organ. Another advantage of the present apparatus over that of U.S. Pat. No. 5,501,652 consists in the fact that the first has only one mirror versus the three mirrors system of the latter, and such a feature results in a lower cost for the apparatus of the invention.

The reflection means 3 with the mirror 5 are also intended for reflecting the image of the external auditory meatus and/or the tympanic membrane in any mirror positioned in front of the subject, for example a wall mirror generally present in any house. The illumination means 6 are suitably made of a lamp 8 equipped with a focalizing lens. which beams a ray light oriented from outside to inside the external auditory meatus such as to effectively illuminate the meatus up to the tympanic membrane too.

As already said, the speculum 2 is pivotally connected, by means of hasps 9, to the box shaped body 4 harboring the mirror 5.

The mirror 5 is preferably harbored in the internal surface of the box shaped body 4 which is suitably in plastic, and its internal surface is made reflecting through well know procedures.

Moreover the surface of the mirror 5 is slightly concave, approximately parabolic, to give the reflected image a suitable magnification factor.

In addition the box shaped body 4 harbors internal power supplying means 11 such as, for example, batteries or a rechargeable battery for feeding the lamp 8. It is furthermore provided a socket 12 for supplying power to the rechargeable battery.

Suitably speculum 2 is removably or fixedly connected to a cover element 13 constituting the covering of the box shaped body 4 when it is closed, and thus making the apparatus of the invention a small box.

In the first embodiment the speculum 2 may be clicked connected to the cover element 13. For making the apparatus of the invention totally closable, the illumination means 6 comprise an armlet supporting the lamp 8 at one end, the other end being pivoted on a side wall of the box shaped body 4, and may rotate to set substantially parallel to the rim of the box shaped body 4 wall.

A suitable hollow 14 is provided in correspondence to such rim for harboring the lamp 8 which is thus turned inward the box shaped body 4, upon the mirror 5.

By this way the cover 13 may perfectly close up the box shaped body 4.

In a variant the armlet is pivoted on the internal part of the side wall of the box shaped body, and by this way the cover 13 may be perfectly closed upon the box shaped 4 without the hollow 14.

Figure 6:
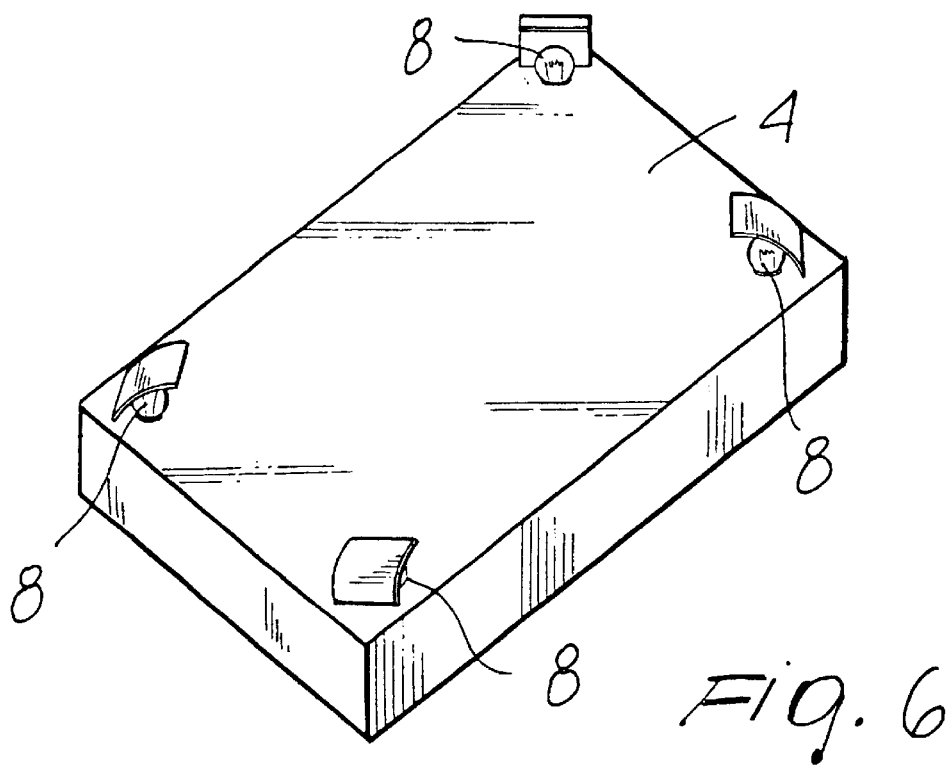
FIGS. 6 and 7 are perspective views of further possible positions of the illumination means of the apparatus according to the present invention.
Figure 7:
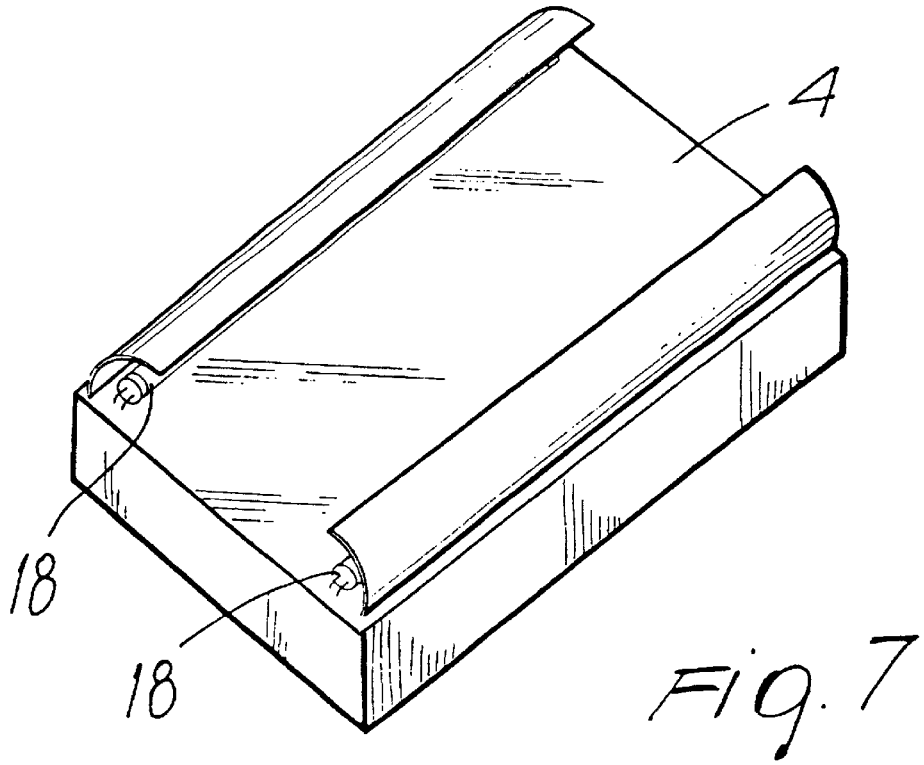

In another variant the light source may be positioned in correspondence to the corners (lamps 8) inside the box shaped body 4, or (neo micro-lamps 18) along the rims of the same (see FIGS. 6 and 7).

The apparatus according to the invention further provides at least a switch for working said apparatus, and such switch may, for example, be directly connected to the opening of the cover 13. By this way, opening the cover 13 the apparatus is automatically put on.

The illumination means 6 together with the relevant lamp 8 are set slightly out of axis with respect to the speculum 2 axis, to suitably reflect the light and not interfere with the image reflected by the mirror 5 coming from the speculum 2.

The hasps 9 permit the reflection means 3 to be suitably angled with respect to the speculum 2 which is inserted in the external auditory meatus of the subject to duly reflect the imagine of the external auditory meatus and/or of the tympanic membrane.

FIG. 2 shows a second embodiment of the apparatus according to the invention, wherein the speculum 2 is pivotally connected to a cylindrical body 20 which is equipped with a mirror 5 having a transparent window 21 inside suitably made, for example, by non metallizing that portion of the mirror 5, and through such window the light is transmitted by illumination means which are then set under the mirror 5 and directly illuminate the external auditory meatus and/or the tympanic membrane. p The illumination means may be analogous to the means illustrated in FIG. 1, i.e. made of one or more lamps 8.

FIG. 3 shows a third embodiment of the apparatus according to the invention, wherein the speculum 2 is fixedly connected to a body substantially having the shape of a frustum of cone, pointed by the reference number 25, harboring a mirror 5 to reflect the images coming from the external auditory meatus and/or the tympanic membrane.

Figure 4B:
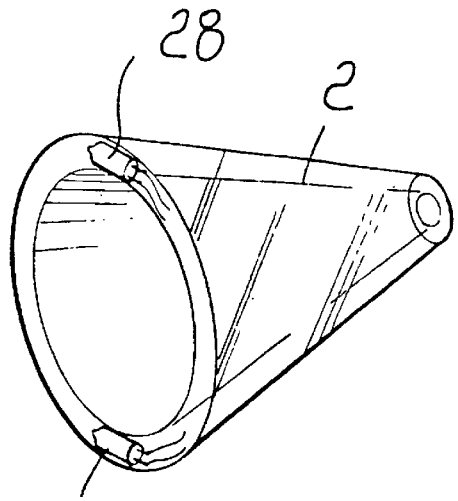
FIG. 4b shows a second variant of the same detail of FIG. 4a, illustrated as assembled in FIG. 3.
Figure 4C:
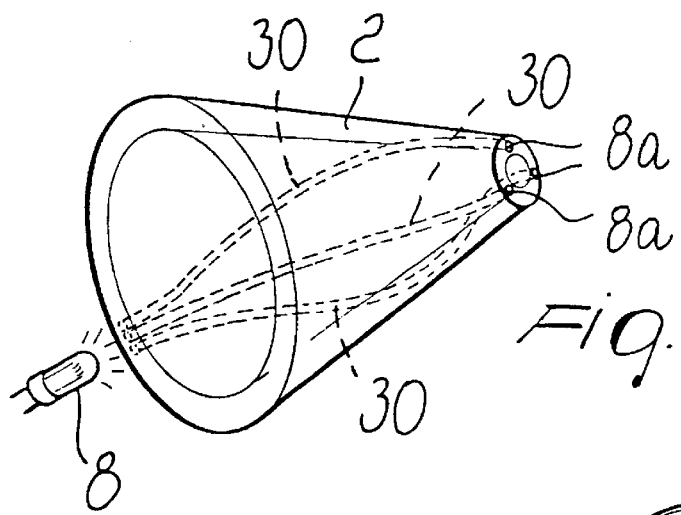
FIG. 4c shows a third variant of the same detail of FIGS. 4a and 4b.

As shown in FIGS. 4a, 4b and 4c, the speculum 2 is suitably equipped with its own illumination means.

As shown in FIGS. 4a, 4b and 4c, for example the illumination means may be made (see FIG. 4a) by a neon microcircle or by an electro-luminescent shaped sheet 26, or, as illustrated in FIG. 4b, by one or more micro-lamps 28 or LED diodes, the speculum 2 being made of a transparent and optically transmitting material.

A third embodiment of the illumination means of the speculum 2 is shown in FIG. 4c, wherein the speculum itself incorporates one or more optical fibers 30 arising in correspondence to the distal part, gathered in correspondence of the lamp 8 and terminating at the opposite end 8a in correspondence of the proximal part of the speculum 2, equally distributed to provide a uniform illumination.

All the illumination systems set forth may be advantageously used in the embodiment of FIG. 3.

Figure 5:
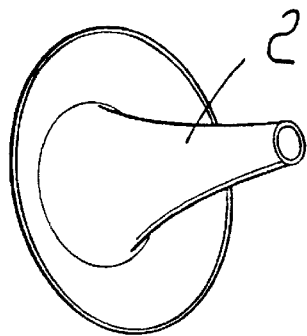
FIG. 5 shows a further embodiment of a portion of the apparatus according to the invention, illustrated in FIGS. 1, 2 and 3.

Finally, FIG. 5 shows a further embodiment of the speculum 2, which can be used in any of the above described embodiments, particularly in that of FIG. 3, wherein the speculum 2 is fixedly connected to the box shaped body. In this case the speculum may be connected to allow an orbital movement, such as it can be suitably angled with respect to the frustum of cone and, as a consequence, with respect to the reflection means, to reflect the image of the external auditor meatus and/or of the tympanic membrane.

The functioning of the apparatus according to the invention is as follows.

The subject wishing inspecting his/her own external auditory meatus and/or the tympanic membrane inserts the speculum 2 into the meatus itself, then suitably angles the mirror 5 thus projecting the image of the external auditory meatus and of the tympanum directly on a mirror in front of him/her, such as, for example, a wall mirror generally present in the houses.

By this way it is possible to effect a self-inspection of the external auditory meatus with no need of specialized centers and persons.

The self-inspection of the external auditory meatus and/or of the tympanic membrane allows to carry out aimed at cleanings and to subsequently check the results. and anyway to control the hygienic conditions.

It has been practically ascertained how the apparatus of the invention fully performs the proposed scope in that it permits the user to carry out an easy, inexpensive and effective self-inspection of his/her own external auditory meatus and/or tympanic membrane with no need of expensive tools and specialized persons.

The so conceived apparatus can be variously modified and varied in manners encircled by the gist of the invention.

Thus, for example, the mirror 5 may be made both in metallized plastic and in common silvery glass.

Moreover the illumination means may produce a white or a colored light, and the emitted ray-light may have, as already said, a direction non coincident to the virtual image axis which is cast back, or coincident to such axis.

The apparatus according to the invention may also be made as a disposable object, and in this case the electrochemical battery is not replaceable.

The socket 12 for connecting battery recharging means may otherwise be used for a source externally fed.

As already said, the illumination means may be made of one or more lamps which can illuminate directly the external auditory meatus under examination, or indirectly the meatus itself following a reflection on the mirror being a part of the apparatus.

Moreover all the details could be substituted by other technically equivalent elements. Practically, the material employed, though compatible with the specific use, and the dimension, may be any according to the requirements and the state of the art.

What is claimed is:

1. Apparatus for self-inspecting one or more anatomical features that include the external auditory meatus and/or the tympanic membrane, comprising a speculum (2) connected to a container (4) comprising a mirror positioned (5) to reflect an image of said external auditory meatus and/or said tympanic membrane, a source of illumination for illuminating said external auditory meatus and/or said tympanic membrane, said mirror being angularly set with respect to said speculum to reflect the image of said external auditory meatus and/or said tympanic membrane on an external mirror, said source of illumination being set over said mirror and including an arm pivotally mounted at one edge of said container (4), and at the other edge that overhangs said mirror (5) at least one lamp (8).

2. Apparatus according to claim 1, wherein the container (4) includes a cover (13) and said speculum (2) is removably connected to the cover.

3. Apparatus according to claim 1, wherein said speculum is movably connected to define orbital movement of the speculum.

4. Apparatus according to claim 1, wherein said speculum (2) is manually positionable inside the auditory meatus.

5. Apparatus according to claim 1 further comprising an internal power supply (11) and an external power supply (12).

6. Apparatus according to claim 1, wherein said mirror (5) has a reflecting surface selected from the group consisting of concave, parabolic and approximately parabolic surfaces.

7. Apparatus according to claim 1, wherein said source of illumination is selected from the group consisting of white light and colored lights.

8. Apparatus according to claim 1, wherein said speculum (2) is made of an optically-transmitting transparent material.

9. Apparatus according to claim 1, wherein said speculum (2) is made of a matte-finished material.

* * * * *